United States Patent [19]

Stout et al.

[11] 4,330,551

[45] May 18, 1982

[54] THERAPEUTIC METHOD

[75] Inventors: Daniel W. Stout, North Palm Beach; Paul R. McGinnes, Lake Park, both of Fla.

[73] Assignee: Synergetics Co.

[21] Appl. No.: 181,464

[22] Filed: Aug. 26, 1980

[51] Int. Cl.³ .................. A61K 27/00; A61K 31/14; A61K 31/40; A61K 31/44; A61K 31/47; A61K 31/415; A61K 31/495

[52] U.S. Cl. ..................... 424/273 R; 424/248.4; 424/248.5; 424/248.57; 424/250; 424/258; 424/263; 424/274; 424/329

[58] Field of Search ............... 424/329, 273, 274, 263, 424/250, 258, 248.4, 248.5, 248.57

*Primary Examiner*—Stanley J. Friedman
*Attorney, Agent, or Firm*—Dressler, Goldsmith, Shore, Sutker & Milnamow, Ltd.

[57] ABSTRACT

Disclosed are therapeutic compositions that comprise an aqueous emulsion constituted by a pharmacologically acceptable cationic surfactant, a pharmacologically acceptable non-ionic surfactant, and water. These compositions are effective in relieving pain, especially high level pain and also for reducing trauma, i.e., for minimizing a wide variety of physiological disorders such as those due to physical injury, abscesses, cysts, and the like. The foregoing compositions contain at least about 5 weight percent of each of the two types of surfactants.

28 Claims, No Drawings

4,330,551

THERAPEUTIC METHOD

TECHNICAL FIELD

This invention relates to therapeutic compositions suitable, inter alia, for pain relief, enhancing the healing of injured tissue, and reduction of swelling and bruises due to trauma, and to methods for treating the foregoing conditions.

BACKGROUND OF THE INVENTION

It is well recognized that the nervous system functions through utilization of positively charged ion systems. That transmitter chemicals are involved in the activity at the synapses of the nervous system is also well documented, as is the effect of metabolic chemicals on the reticuloendothelial system.

Trauma or stress, whether occasioned through accident or disease, is believed to have a direct effect on the ever present ionic activity within the system. Some of the manifestations of trauma include moderately severe, or severe acute and chronic pain. Other manifestations are muscle spasms, stiffness, or even partial or complete immobilization. Additionally, certain metabolic products may undergo a change, e.g., may polarize or crystallize, within the system when the body is subjected to trauma, which change may interfere with the normal transport mechanisms for such metabolic products within the system.

Anesthetic and analgesic agents of various kinds have been used since ancient times for pain relief. Such agents include a wide variety of chemical substances, e.g., the narcotics, the inhalation anesthetics such as nitrous oxide and ether, as well as the local anesthetics, such as cocaine, procaine, and a large number of synthetic compounds.

In general, the commonly known local anesthetics include a hydrophilic amino group which is connected to a lipophilic aromatic residue by an intermediate chain constituted by an amide bond as in lidocaine and dibucaine or by an ester link as in procaine. The general properties of commonly known local anesthetics are described in Goodman and Gilman, *The Pharmacological Basis of Therapeutics*, 3d ed., The Macmillan Co., New York, New York, 1965, pp. 367 et seq. While much research has been carried out since 1965, the mechanism or mechanisms of anesthetic action are still not thoroughly understood.

It has now been discovered that aqueous emulsions of certain cationic surfactants in combination with certain non-ionic surfactants provide unexpectedly effective pain relief, especially in case of moderate and high level pain, and reduce trauma, e.g., accelerate the healing and regeneration of damaged tissue. In particular, the present compositions are useful for alleviating pain associated with migraine headache, non-specific high level pain headache, arthritis, burns, spinal and orthopedic disorders, physical injuries, surgical procedures, gastritis, diverticulitis, boils, toothache, shingles, and similar physical disorders.

Additionally, it has been found that the administration of the present compositions to a patient provides beneficial ancillary effects, such as increased blood circulation in the traumatized region, relief of semiparalytic conditions, rapid tissue healing (especially in case of burns and deep cuts) and regeneration of damaged tissue, absorption of boils and abscesses, regeneration of small nerve networks including the enhancement of sensory transmission in surgically severed nerves, absorption of cysts such as ganglionic cysts, increased mobility and flexibility of arthritic joints, relaxation of muscle cramps and spasms, and the like. The compositions and methods of the present invention are also effective in reducing shock due to an accident, swelling and discoloration due to trauma, and chronic skin seborrhea.

The present invention is of particular value in that it appears not to function by removing complete sensory perception of the injury or trauma, but rather functions to bring about the absence of perception of high level pain. Although pain is of necessity subjective, high level pain can be regarded as that which causes incapacitation of function as in major arthritis pain, migraine headaches, or that for which narcotics are frequently prescribed.

SUMMARY OF THE INVENTION

Therapeutic compositions contemplated by the present invention comprise an aqueous emulsion constituted by a pharmacologically acceptable cationic surfactant, a pharmacologically acceptable non-ionic surfactant and water. The co-action of these two types of surfactants provides synergistic therapeutic benefits. The present compositions are suitable for relief from pain, and for reducing trauma, that is, for minimizing a wide variety of physiological disorders such as those due to physical injury, abscesses, cysts, and the like.

The aqueous emulsion contains at least about 5 weight percent of each of the two types of surfactants. The water content of the emulsion is at least about 10 percent by weight, preferably about 30 to about 90 percent by weight. More preferably, the present compositions contain about 15 to about 35 weight percent of the cationic surfactant, about 15 to about 35 weight percent of the non-ionic surfactant, and about 70 to about 50 weight percent water.

The emulsion is prepared by admixing the surfactants with water and heating while the resulting admixture is agitated to produce a smooth emulsion.

When treating a patient, an effective amount of the present composition is administered topically as an ointment or spray, as an impregnated bandage, or in like manner. Additionally, administration may be effected by ingestion or injection in appropriate cases.

DESCRIPTION OF PREFERRED EMBODIMENTS

The present compositions are aqueous emulsions that contain as essential ingredients, a nitrogenous or other cationic surfactant that is pharmacologically acceptable, a non-ionic surfactant that is pharmacologically acceptable, and water. If desired, the composition may contain additional secondary ingredients such as common, low level analgesics, for example, aspirin, triethanolamine salicylate, ethylaminobenzoate, etc., astringents, antiseptics, antibiotics, bacteriocides, fungicides, neurologically active or system-specific drugs and remedies, moisturizers, emollients, perfumes, coloring agents, and the like.

Quadricovalent nitrogen-containing cationic surfactants suitable for the present purposes are the quaternary ammonium salts of pharmacologically acceptable, non-toxic acids. These quaternary ammonium salts are represented by the general formula

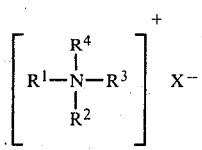

wherein
R[1], R[2], R[3] and R[4] are organic groups which can be alike or different, and
X[-] is an anion of a pharmacologically acceptable acid.

Any two or more of the R[1], R[2], R[3] and R[4] groups together with the depicted nitrogen atom may also form a polyvalent group which is part of a cyclic structure that includes the nitrogen atom. Examples of such cyclic structures are imidazolinium, pyridinium, morpholinium, piperazinium, pyrrolidinium, quinolinium, and the like.

Illustrative monovalent R[1], R[2], R[3] and R[4] groups are aliphatic or aromatic groups containing up to 22 carbon atoms such as $C_1$ to $C_{22}$ alkyl groups, e.g., methyl, ethyl, propyl, n-butyl, n-octyl, n-decyl, n-dodecyl, n-cetyl, stearyl, hydrogenerated tallow fatty radicals,; $C_1$ to $C_{22}$ aralkyl groups, e.g., benzyl, ethylbenzyl, dodecylbenzyl; polyoxyalkylene groups, e.g., polyoxypropylene chains, polyoxyethylene chains; $C_1$ to $C_{22}$ alkenyl groups, e.g., 1-propenyl, 2-butenyl, 2-pentenyl.

Illustrative anions within the purview of the X[-] group are the halides e.g., chloride, bromide, iodide, fluoride; acetate; nitrite; the ortho-, meta- and pyrophosphates; sulfate; the $C_1$ to $C_4$ alkylsulfates, e.g., methylsulfate, ethylsulfate; and the like.

Typical nitrogenous cationic surfactants within the purview of the foregoing definition are:
distearyl dimethyl ammonium chloride,
polyoxypropylene (9) methyl diethyl ammonium chloride,
didecyl dimethyl ammonium chloride,
cetyl dimethyl ethyl ammonium bromide,
dimethyl di(hydrogenated tallow) ammonium chloride,
dicoco dimethyl ammonium chloride,
dimethyl hydroxyethyl cetyl ammonium chloride,
dimethyl dilauryl ammonium chloride,
ditallow dimethyl ammonium chloride,
1-methyl-1-[2-(hydrogenated tallow) amidoethyl]-2-hydrogenated tallow imidazolinium methyl sulfate,
di(hydrogenated tallow) dimethyl ammonium methyl sulfate,
di(hydrogenated tallow) dimethyl ammonium chloride,
ethyl bis(polyhydroxyethyl)alkyl ammonium ethyl sulfate,
dimethyl stearyl benzyl ammonium chloride.

For the present compositions preferred are the quaternary ammonium compounds wherein R[1] and R[3] are alkyl groups containing 12 to 18 carbon atoms and R[2] and R[4] are lower alkyl groups containing 1 to 4 carbon atoms.

The non-ionic surfactants suitable for compounding the present therapeutic compositions are organic compounds of a relatively high molecular weight and constituted by a hydrophobic-lopophilic portion to which is attached a solubilizing or hydrophilic-lipophobic portion containing one or more groups such as ether links (—C—O—C—), hydroxyl groups (—OH), carbonyloxy groups

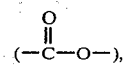

and the like. These compounds preferably have a hydrophilic-lipophilic balance index (HLB Index) of about 2 to about 20. For present purposes more preferred are those non-ionic surfactants having a HLB Index of about 2 to about 7, i.e., the less water-soluble surfactants.

Non-ionic surfactants preferred for compounding the present therapeutic compositions are esters, ethers, or both, derived from: (1) a mono- or polyhydric alcohol and one or more fatty acids, preferably long chain saturated fatty acids, (2) a mono- or polyhydric alcohol etherified with an alkylene oxide to produce an alkyleneoxy chain-containing compound, or (3) a fatty acid esterified with the aforesaid alkyleneoxy chain-containing compounds. Such surfactants can be represented by the general formula $$R^5\text{-}Y$$

wherein
$R^5$ is the hydrophobic-lipophilic portion of an aliphatic alcohol containing about 6 to about 22 carbon atoms or a $C_{10}$ to $C_{20}$ fatty acid residue, and
Y is a hydrophilic-lipophobic portion, typically an alkyleneoxy chain terminated by a hydrogen atom bonded to an oxygen atom of the alkyleneoxy chain or a polyhydric alcohol anhydride.

Illustrative aliphatic alcohols are octyl alcohol, sorbitol, mannitol, nonyl alcohol, decyl alcohol, "coco" alcohol (a mixture of $C_{10}$ to $C_{16}$ alcohols), dodecyl alcohol, oleyl alcohol, tallow alcohol (a mixture of $C_{16}$ to $C_{18}$ alcohols), octadecyl alcohol, 2,6,8-trimethyl-4-nonyl alcohol, the synthetic fatty alcohols, and the like.

The polyhydric alcohol anhydride is a cyclic dehydration product of a polyhydric alcohol, e.g. hexitol anhydride, and the like.

The term "alkyleneoxy chain", as used herein, is intended to mean a chain containing one or more alkyleneoxy groups which ae divalent alkylene groups, e.g., ethylene, propylene, butylene, bonded to an oxygen atom in a manner such that one of the valences of the alkyleneoxy group is from an oxygen atom and the other is from a carbon atom. Illustrative alkyleneoxy groups are ethyleneoxy (—$C_2H_4O$—), propyleneoxy (—$C_3H_6O$—), and butyleneoxy (—$C_4H_8O$—). Preferred for the present compositions are alkyleneoxy chain-containing non-ionic surfactants containing about 8 to about 30 moles of alkylene oxide per molecule.

Particularly preferred for the present purposes are non-ionic surfactants that are long chain saturated fatty acids esterified with a polyhydric alcohol anhydride, i.e., the sorbitan esters. That is, the reaction products of hexitol anhydride with long chain saturated fatty acids such as stearic acid, palmitic acid, lauric acid, and the like, with an alkyleneoxy chain, or with both of the foregoing.

Illustrative non-ionic surfactants suitable for utilization in the present compositions are:
sorbitan monopalmitate,
polyoxyethylene (20) sorbitan monopalmitate,
polyoxyethlene (8) stearate,
polyoxyethylene (25) propylene glycol stearate,
sorbitan monostearate, polyoxyethylene (2) cetyl ether.

Compositions embodying the present invention contain at least about 5 weight percent of the cationic surfactant and at least about 5 weight percent of the non-ionic surfactant. Preferably the weight ratio of cationic surfactant-to-non-ionic surfactant is about 1:1; however, the ratio can vary from about 3:1 to about 1:3.

Water content of the present compositions is at least about 10 percent by weight, preferably about 30 to about 90 percent by weight. More preferably, the water content of the present compositions is about 50 to about 70 percent by weight.

Typical illustrative formulations embodying the present invention are set forth hereinbelow in Table I.

TABLE I

THERAPEUTIC COMPOSITIONS

| | Parts by weight |
|---|---|
| Formulation I | |
| sorbitan monopalmitate | 25 |
| di(hydrogenated tallow) dimethyl ammonium methyl sulfate | 25 |
| distilled water | 50 |
| | 100 |
| Formulation II | |
| polyoxyethylene (20) sorbitan monopalmitate | 35 |
| di(hydrogenated tallow) dimethyl ammonium methyl sulfate | 35 |
| distilled water | 30 |
| | 100 |
| Formulation III | |
| polyoxyethylene (8) stearate | 30 |
| di(hydrogenated tallow) dimethyl ammonium methyl sulfate | 30 |
| distilled water | 40 |
| | 100 |
| Formulation IV | |
| polyoxyethylene (25) propylene glycol stearate | 35 |
| di(hydrogenated tallow) dimethyl ammonium chloride | 35 |
| distilled water | 30 |
| | 100 |
| Formulation V | |
| sorbitan monostearate | 30 |
| ethyl bis(polyhydroxyethyl)alkyl ammonium ethyl sulfate | 30 |
| distilled water | 40 |
| | 100 |
| Formulation VI | |
| sorbitan monostearate | 30 |
| dimethyl stearyl benzyl ammonium chloride | 30 |
| distilled water | 40 |
| | 100 |
| Formulation VII | |
| sorbitan monopalmitate | 25 |
| di(hydrogenated tallow) dimethyl ammonium chloride | 25 |
| distilled water | 50 |
| | 100 |
| Formulation VIII | |
| sorbitan monopalmitate | 27.5 |
| 1-methyl-1-[2-(hydrogenated tallow)-amidoethyl]-2-hydrogenated tallow imidazolinium methyl sulfate | 27.5 |
| distilled water | 45 |
| | 100 |
| Formulation IX | |
| polyoxyethylene (2) cetyl ether | 20 |
| di (hydrogenated tallow) dimethyl ammonium chloride | 20 |
| distilled water | 60 |
| | 100 |

TABLE I-continued

THERAPEUTIC COMPOSITIONS

| | Parts by weight |
|---|---|
| Formulation X | |
| polyoxyethylene (2) cetyl ether | 18 |
| 1-methyl-1-[2-(hydrogenated tallow)-amidoethyl]-2-hydrogenated tallow imidazolinium methyl sulfate | 18 |
| distilled water | 64 |
| | 100 |

The compositions are compounded by combining the two types of surfactants with water, e.g., distilled water or deionized water, and then stirring while the produced admixture is heated to produce a smooth emulsion. More specifically, the two surfactants are added to a suitable container or vessel and a sufficient portion of distilled water is added to formulate the emulsion having the desired water content and allow for evaporation during mixing. The materials are mixed by stirring continuously while heat is applied to the container. The resulting mixture is heated until the melting point of the highest constituent present is reached. At that point, stirring is continued until a smooth uniform emulsion is obtained that remains substantially homogenous upon subsequent cooling. Thereafter the produced emulsion is cooled to ambient temperature and is ready for use.

The compositions of this invention are administered to a patient suffering pain by applying to the affected body region a pain-relieving amount of the composition. For topical application as an ointment or lotion, the composition is applied and preferably rubbed lightly until the composition is absorbed into the skin, preferably in an amount that is absorbed at the application site within a time period of about one minute or less. When the composition is applied topically as a solid mass or impregnated into a carrier such as a bandage, the composition preferably is lightly rubbed over the afflicted area and then positioned in place to permit absorption of the active ingredients over an extended period of time. Moreover, it has been observed that the applied compositions exhibit a residual effect as well, i.e., pain relief in a region to which the composition had been applied previously can be reactivated by light massage with a damp cloth or the like.

In the case of trauma, the more rapid the application of the composition to the traumatized region after the injury, the more dramatic and effective the ultimate recovery. Preferably the initial application of the composition is effected in such cases no later than about four hours after the injury.

The beneficial effects other than the relief of pain afforded by the present compositions are also important. Indications of the recovery of use in partial paralysis or where small nerves have been surgically severed have been obtained, as has evidence of increased muscle tone. The rehabilitation of some disabled individuals to the point that they have been able to return to their normal occupation has also been attributed to the use of this invention.

Efficacy of compositions embodying the present invention is illustrated by the case histories set forth hereinbelow.

CASE HISTORY #1

A female patient in her mid-30's with a history of ganglionic cysts in her wrist continuously over the previous twenty years was treated with an aqueous emulsion constituted as set forth in Formulation I. Prior to the present treatment it had been necessary to either remove the cyst surgically or to forcefully rupture the cyst by a blow. At the time of treatment, the patient's cyst distended above the skin approximately 8 millimeters and had an apparent diameter of 15 to 20 millimeters. Upon topical application of the aforesaid aqueous emulsion in an amount that was absorbed within about 30 seconds, the patient reported a tingling sensation in the wrist and forearm. Within 24 hours of the application, the cyst had diminished in size, and within 48 hours had disappeared completely. At that time, a complete restoration of use of the wrist was observed. After a period of six weeks from the application, no indication of the cyst's recurrence has been observed.

CASE HISTORY #2

A female patient (age 62) with recurring osteoarthritis in her right thumb and wrist for the last three years and reporting both pain and a lack of flexibility in the affected joints, was treated by applying the composition of Formulation I topically to the right thumb and the wrist in an amount that was absorbed in about 30 seconds. Substantial immediate relief from pain, commencing within ten seconds of application and lasting several days, was reported by the patient. Subsequently the patient reported that all pain had disappeared. Complete flexibility of the affected joints was restored.

CASE HISTORY #3

A female patient in her mid-30's received a severe searing burn on two fingers and was treated with the composition of Formulation VII. The composition was applied immediately to the burn region and some temporary pain relief was noted. To maintain pain relief, repeated applications over the next several hours were required. Approximately two hours after the composition was applied, pain relief was virtually complete. Further topical applications of the composition were discontinued at that time. The burn was virtually healed after about 24 hours, displaying only a slight glazing of the surface of the skin at the site of the burn. Complete flexibility of the skin was restored and no further pain was reported. Within 72 hours after commencement of the treatment, the burn was completely healed, and the site of the burn could not be identified by visual inspection.

CASE HISTORY #4

A female child (age 11) received a hard blow to the cheekbone immediately under the right eye. The right eye started to swell and discolor almost immediately. The composition of Formulation I was applied topically to the discolored region within five minutes of receiving the blow and in an amount that was absorbed within about 60 seconds. The swelling ceased, and the sharp pain associated with the blow was alleviated almost immediately. Over the next 72 hours no swelling was observed, and no discoloration was observed except in the immediate area of the eyelid where the composition was not applied. The patient did complain of a soreness or ache around the eye area for at least 72 hours, although no severe pain was reported.

CASE HISTORY #5

A female child (age 8), of very fair complexion, received a severe sunburn and was complaining of severe discomfort. Redness of the skin and some blistering were observed to be present in the sunburned areas. The composition of Formulation I was applied to the sunburned area. Within two hours pain relief was reported, and the blistering had disappeared. After spending a night with no apparent discomfort, the next morning the child did not show any signs of severe sunburn but appeared to be tanned. No discomfort due to sunburn was reported at that time.

CASE HISTORY #6

A female patient in her early 20's complained of acute abdominal pain following a meal. Two or three hours after the complaint, the composition of Formulation I was topically applied to the abdominal area in an amount that was absorbed in about 60 seconds. Pain relief within seconds was reported. No recurrence of the discomfort was reported.

CASE HISTORY #7

A female patient in her mid-70's who is a retired registered nurse was confined to her home for the last seven years, much of that time being bed confinement, due to extreme pain and loss of mobility from multiple whiplash injuries, a surgically implanted plate repairing a skull fracture, and resulting migraine headaches. The patient was treated with the composition of Formulation I, which had been applied to a bandage and allowed to dry. The impregnated bandage was used to rub the affected areas and provided relief of severe head pains within two minutes upon the initial application. Subsequent treatments have relieved both the pain from migraine and whiplash completely over the last ten-month period of time.

CASE HISTORY #8

A male patient in his early 60's with crushed fifth and sixth cervical discs with bone spurs and extreme pain in the cervical area, a lack of mobility of the head and neck, and semi-paralysis of the right arm was treated with Formulation VII. The formulation was rubbed into the neck, shoulder and wrist. The patient has recovered full use of his right arm, has had virtually full recovery of the mobility of his head and neck, and has experienced relief from almost all pain. Some soreness and low level aches still persist. The relief from pain and restoration of mobility has now been maintained over a period of ten months, although X-rays indicate no structural changes in the discs or vertebrae.

CASE HISTORY #9

A male patient in his late 30's with injuries suffered in an automobile accident (a broken neck, a back broken in two places, a severly damaged right knee, and some paralysis of the left leg) was treated in accordance with the present invention. The injuries sustained resulted in severely limited mobility and considerable pain even after the injuries had nominally healed. The composition of Formulation I was applied to the affected and painful areas. Relief from the pain was reported in approximately fifteen minutes after the application. The patient is maintaining treatment by applying Formulation I once a week to the affected areas. The knee, back and neck pains have been relieved, and the semi-paralysis of the left leg has disappeared.

CASE HISTORY #10

A male patient in his 40's experienced knee surgery in which cartilage was surgically removed, and one nerve to the knee was severed. Since the surgery, the patient has complained of continually chronic severe pain in the knee for the past two and one-half years. An application of the composition of Formulation VII to the painful area provided total relief from the pain in less than ten minutes. The patient has reported absence of pain, restoration of mobility in the leg on a continuous basis while applying the formulation approximately once a week.

CASE HISTORY #11

A male approximately 90 years old suffered a backwards fall which resulted in severe contusions, a laceration of the head, and cracked fractures of the shoulder blade and shoulder joint. Immediate swelling of the shoulder was noted and intense pain in both the shoulder and head were reported. The composition of Formulation I was applied topically to the shoulder very soon after the injury was sustained. The injuries were subsequently treated in a hospital emergency room, the laceration was sutured, and X-rays of the shoulder were taken. Within 24 hours the patient reported that he was experiencing no pain from his shoulder, and experienced difficulty only when he attempted to raise his arm over his head. There was no noticeable swelling or discoloration in the shoulder area. The patient wore a sling that was provided in the emergency room for about 24 hours and thereafter discarded it.

CASE HISTORY #12

A female patient (age 80) has been diagnosed as having a rapidly progressing pancreatic cancer. This type of cancer produces extreme pain and no conventional method of treatment for pain has been found effective for this patient. The material in Formulation VIII was applied to the patient's abdomen topically in the general area of the pancreas. The pain was relieved within 15 minutes, and pain relief continued for a period of two and one-half to five and one-half hours, depending on the patient's activity and eating schedule. When the pain does recur, a new topical application of the composition of Formulation VIII has provided pain relief for an additional period of time. In addition, pain relief for a relatively shorter time period was obtained by applying wet heat to the previously treated region.

The foregoing discussion and the specific formulations recited are illustrative and are not to be taken as limiting, since, for example, substitution of constituents, variations in the relative amounts thereof, and/or varying concentrations thereof are possible without departing from the spirit and scope of the present invention.

What is claimed is:

1. A method of treating a patient afflicted with pain which comprises administering to the patient as the sole pain-relieving constituent a pain-relieving amount of an aqueous emulsion comprising a pharmacologically acceptable cationic surfactant, a pharmacologically acceptable non-ionic surfactant, and water; said emulsion containing at least about 5 weight percent of said cationic surfactant and at least about 5 weight percent of said non-ionic surfactant.

2. The method in accordance with claim 1 wherein said aqueous emulsion contains about equal amounts of said cationic surfactant and said non-ionic surfactant.

3. The method in accordance with claim 1 wherein said aqueous emulsion contains about 15 to about 35 weight percent of said cationic surfactant and about 15 to about 35 weight percent of said non-ionic surfactant, and about 50 to about 30 weight percent water.

4. The method in accordance with claim 1 wherein said cationic surfactant is represented by the general formula

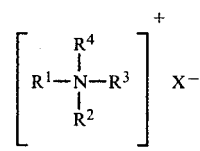

wherein
each of $R^1$, $R^2$, $R^3$ and $R^4$ is a monovalent organic group or at least two of said $R^1$, $R^2$, $R^3$ and $R^4$ together form part of a cyclic structure, and
$X^-$ is an anion of a pharmacologically acceptable acid.

5. The method in accordance with claim 4 wherein $R^1$ and $R^3$ are alkyl groups of 12 to 18 carbon atoms and $R^2$ and $R^4$ are lower alkyl groups of 1 to 4 carbon atoms.

6. The method in accordance with claim 1 wherein the cationic surfactant is a long chain saturated fatty acid ester of a polyhydric alcohol anhydride.

7. The method in accordance with claim 1 wherein the cationic surfactant is di(hydrogenated tallow) dimethyl ammonium methyl sulfate and the non-ionic surfactant is sorbitan monopalmitate.

8. The method in accordance with claim 1 wherein the cationic surfactant is di(hydrogenated tallow) dimethyl ammonium chloride and the non-ionic surfactant is polyoxyethylene (2) cetyl ether.

9. The method in accordance with claim 1 wherein the cationic surfactant is 1-methyl-1-[2-(hydrogenated tallow) amidoethyl]-2-hydrogenated tallow imidazolinium methyl sulfate and the non-ionic surfactant is polyoxyethylene (2) cetyl ether.

10. The method in accordance with claim 1 wherein the cationic surfactant is ethyl bis(polyhydroxyethyl) alkyl ammonium ethyl sulfate and the non-ionic surfactant is sorbitan monostearate.

11. The method in accordance with claim 1 wherein the cationic surfactant is dimethyl stearyl benzyl ammonium chloride and the non-ionic surfactant is sorbitan monostearate.

12. The method in accordance with claim 1 wherein the cationic surfactant is di(hydrogenated tallow) dimethyl ammonium chloride and the non-ionic surfactant is sorbitan monopalmitate.

13. The method in accordance with claim 1 wherein the cationic surfactant is 1-methyl-1-[2-(hydrogenated tallow) amidoethyl]-2-hydrogenated tallow imidazolinium methyl sulfate and the non-ionic surfactant is sorbitan monopalmitate.

14. The method in accordance with claim 1 wherein the aqueous emulsion is administered by topical application to the skin of the patient.

15. A method of reducing trauma which comprises applying to a traumatized region of a patient an effective amount of an aqueous emulsion comprising a pharmacologically acceptable nitrogenous cationic surfactant, a pharmacologically acceptable non-ionic surfactant, and water; said emulsion containing at least about 5 weight percent of said cationic surfactant and at least about 5 weight percent of said non-ionic surfactant.

16. The method in accordance with claim 15 wherein said aqueous emulsion contains about equal amounts of said cationic surfactant and said non-ionic surfactant.

17. The method in accordance with claim 15 wherein said aqueous emulsion contains about 15 to about 35 weight percent of said cationic surfactant and about 15 to about 35 weight percent of said non-ionic surfactant, and about 50 to about 30 weight percent water.

18. The method in accordance with claim 15 wherein said cationic surfactant is represented by the general formula

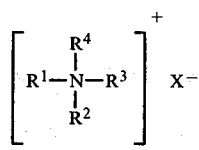

wherein
each of $R^1$, $R^2$, $R^3$ and $R^4$ is a monovalent organic group or at least two of said $R^1$, $R^2$, $R^3$ and $R^4$ together form part of a cyclic structure, and
$X^-$ is an anion of a pharmacologically acceptable acid.

19. The method in accordance with claim 18 wherein $R^1$ and $R^3$ are alkyl groups of 12 to 18 carbon atoms and $R^2$ and $R^4$ are lower alkyl groups of 1 to 4 carbon atoms.

20. The method in accordance with claim 15 wherein the non-ionic surfactant is a long chain saturated fatty acid ester of a polyhydric alcohol anhydride.

21. The method in accordance with claim 15 wherein the cationic surfactant is di(hydrogenated tallow) dimethyl ammonium methyl sulfate and the non-ionic surfactant is sorbitan monopalmitate.

22. The method in accordance with claim 15 wherein the cationic surfactant is di(hydrogenated tallow) dimethyl ammonium chloride and the non-ionic surfactant is polyoxyethylene (2) cetyl ether.

23. The method in accordance with claim 15 wherein the cationic surfactant is 1-methyl-1-[2-(hydrogenated tallow) amidoethyl]-2-hydrogenated tallow imidazolinium methyl sulfate and the non-ionic surfactant is polyoxyethylene (2) cetyl ether.

24. The method in accordance with claim 15 wherein the cationic surfactant is ethyl bis(polyhydroxyethyl) alkyl ammonium ethyl sulfate and the non-ionic surfactant is sorbitan monostearate.

25. The method in accordance with claim 15 wherein the cationic surfactant is dimethyl stearyl benzyl ammonium chloride and the non-ionic surfactant is sorbitan monostearate.

26. The method in accordance with claim 15 wherein the cationic surfactant is di(hydrogenated tallow) dimethyl ammonium chloride and the non-ionic surfactant is sorbitan monopalmitate.

27. The method in accordance with claim 15 wherein the cationic surfactant is 1-methyl-1-[2-(hydrogenated tallow) amidoethyl]-2-hydrogenated tallow imidazolinium methyl sulfate and the non-ionic surfactant is sorbitan monopalmitate.

28. The method in accordance with claim 15 wherein the aqueous emulsion is administered by topical application to the skin of the patient.

* * * * *